United States Patent [19]

Shah et al.

[11] Patent Number: 5,219,877
[45] Date of Patent: Jun. 15, 1993

[54] LAURYL ALCOHOL AS SKIN PENETRATION ENHANCER FOR TOPICAL IMIDAZOLE AGENTS

[75] Inventors: Hemanshu S. Shah, Williamsville; Susan Genier, Buffalo; Cheng D. Yu, Tonawanda; Bhiku Patel, Amherst, all of N.Y.

[73] Assignee: Bristol-Myers Squibb Company, New York, N.Y.

[21] Appl. No.: 413,363

[22] Filed: Sep. 25, 1989

[51] Int. Cl.$^5$ ............................................. A61K 31/415
[52] U.S. Cl. .................................... 514/399; 514/396; 514/947
[58] Field of Search ........................ 514/396, 399, 947

[56] References Cited

U.S. PATENT DOCUMENTS

| | | | |
|---|---|---|---|
| 4,038,409 | 7/1977 | Walker et al. | 514/399 |
| 4,299,826 | 11/1981 | Luedders | 424/181 |
| 4,752,612 | 6/1988 | Saito et al. | 514/420 |

FOREIGN PATENT DOCUMENTS 1518683  3/1978  United Kingdom .

OTHER PUBLICATIONS

Mollgaard et al., *Acta Pharm. Suec.* 20, 443–450 (1983).
Yamada et al., *Chem. Pharm. Bull.*, vol. 35 (8), 3390–3398 (1987).
Aungst et al., *Int. J. Pharm.*, 33, 225–234 (1986).
Tsuzuki et al., *Int. J. Pharm.* 46, 19–23 (1988).
Akazawa et al., *Int. J. Pharm.*, 50, 53–60 (1989).
Bhatt et al., *Int. J. Pharm.*, 50, 197–203 (1989).

*Primary Examiner*—Leonard Schenkman
*Attorney, Agent, or Firm*—Sandra M. Nolan

[57] ABSTRACT

A gel formulation for topical administration with enhanced skin penetration properties comprising a therapeutically effective amount of an imidazole antifungal agent, either by itself or in combination with a steroid anti-inflammatory agent, in a vehicle system that includes lauryl alcohol is disclosed.

22 Claims, 3 Drawing Sheets

LAURYL ALCOHOL AS SKIN PENETRATION ENHANCER FOR TOPICAL IMIDAZOLE AGENTS

BACKGROUND OF THE INVENTION

The present invention relates to a stable, lauryl alcohol containing formulation having superior skin penetration properties and improved antifungal properties for the topical application of an imidazole antifungal agent either by itself or in combination with a steroid anti-inflammatory agent. The produce is particularly suitable for treating fungal diseases such as tinea capitis, tinea corporis, tinea cruris, tinea pedis, tinea versicolor or cutaneous candidiasis.

A fungus is a very small microscopic type of plant cell which may grow on the skin and, under certain conditions, produce an infection. Such fungi-caused infections, the mycoses, are among the oldest known to man and have long been recognized as a highly prevalent health problem.

A variety of methods have been used for the treatment of fungal infections including the use of potassium iodide, Whitfield's ointment, undecylenic acid, antibiotics (e.g., nystatin and amphotericin B), griseofulvin and imidazole antifungal agents such as miconazole, clotrimazole, econazole and sulconazole. The imidazoles were the first broad-spectrum antifungals and are of considerable importance in clinical practice. Their broad spectrum of antifungal activity, extending to most pathogenic fungi, has provided an important advance in antifungal therapy.

Recently, it has been found that fungal infections can be effectively treated with a combination product containing corticosteroid anti-inflammatory agents and imidazole antifungal agents. Currently, the commercially available combination products using this concept are Lotrisone cream (clotrimazole 1%/betamethasone dipropionate 0.05%), Daktacort cream (miconazole nitrate 2%/hydrocortisone 1%) and Canesten HC cream (clotrimazole 1%/hydrocortisone 1%). Katz et al, Cutis 34, 183 (1984) and Wortzel, Cutis 30, 258 (1982) found that Lotrisone cream was therapeutically and mycologically better than clotrimazole 1% and betamethasone dipropionate 0.05% alone.

To be optimally effective, the imidazole antifungal agent and steroid anti-inflammatory agent must be brought into direct contact with the fungal infection being treated. Unfortunately, such infections are frequently located in hard-to-reach deeper skin layers, hyper-keratinized skin and/or nails. Hence, it would be desirable to have an imidazole antifungal agent, either by itself or in combination with a steroid anti-inflammatory agent, formulated in a vehicle having a high degree of skin penetration, enabling it to reach hard-to-reach fungal infections.

There is considerable literature on the use of permeation/penetration enhancers to increase the penetration of drug molecules into or through the skin. U.S. Pat. No. 4,775,678, Su et al, issued Oct. 4, 1988 discloses the use of a combination of petrolatum, a bodying agent such as cetyl alcohol, stearyl alcohol, cetearyl alcohol (a mixture of cetyl alcohol and stearyl alcohol) or stearic acid, and a solubility enhancer such as propylene glycol, hexylene glycol, or polyethylene glycol as a penetration enhancer for a clotrimazole-containing cream base.

U.S. Pat. No. 4,552,872, Cooper et al, issued Nov. 12, 1985 discloses the use of a diol and a cell-envelope disordering compound such as methyl laurate, oleic acid, and myristyl alcohol as a penetration enhancer for a corticosteroid.

Similarly, U.S. Pat. No. 4,537,776, Cooper et al, issued Aug. 27, 1985, discloses a penetration-enhancing vehicle for pharmaceutically-active agents consisting essentially of N-(2-hydroxyethyl)pyrrolidone and a cell-envelope disordering compound.

Cooper et al, J. Pharm. Sci. 74, 688–689 (1985) describe the use of oleic acid and oleyl alcohol as penetration enhancers for acyclovir.

Lauryl alcohol (1-dodecanol) has been found to be a skin penetration enhancer for several pharmaceutical agents.

Yamada et al in Chem. Pharm. Bull. vol. 35 (8), 3390–3398 (1987) disclose the effectiveness of lauryl alcohol as an absorption enhancer for molsidomine L (N-ethoxycarbonyl-3-morpholinosydononimine).

Aungst et al in Int. J. Pharm. 33, 225–234 (1986) disclose the effectiveness of lauryl alcohol and lauric acid as potent agents for increasing the skin penetration of naloxone.

Tsuzuki et al, Int. J. Pharm. 46, 19–23 (1988) disclose the effectiveness of lauryl alcohol as a penetration enhancer for indomethacin through shed snake skin.

U.S. Pat. No. 4,752,612, Saito, issued Jun. 21, 1988 discloses a method of percutaneously administering a non-steroid anti-inflammatory agent wherein the carrier system comprises a $C_{10}$–$C_{26}$ aliphatic monoalcohol and a pyrrolidone-type solvent.

In Akazawa, Int. J. Pharm. 50 (1989) 53–60, lauryl alcohol was used with minoxidil and benzocaine in test formulations for evaluating an automated diffusion cell apparatus.

U.S. Pat. No. 4,299,826, Luedders, issued Nov. 10, 1981 discloses the use of lauryl alcohol as a penetration enhancer for erythromycin.

In Bhatt, Int. J. Pharm. 50 (1989) 197–203, lauryl alcohol was used with propylene glycol and acetaminophen in a test formulation for experiments directed towards developing a theoretical model for the transport of drugs across the stratum corneum.

British Pat. No. 1,518,683 (1978) discloses a skin permeation preparation comprising a pharmaceutically active agent at least partially dissolved in a carrier material mixture comprising at least one skin-compatible aliphatic $C_{11}$ to $C_{25}$ alcohol and one skin-compatible anionic and/or amphoteric tenside, such as a salt of a dialkanolamine or trialkanolamine.

In Mollgaard et al, Acta Pharm. Suec. 20 (1983) 443–450, it was found that the skin permeation of metronidazole, an imidazole, in propylene glycol was increased in vehicles containing $C_8$, $C_{10}$ or $C_{12}$ alkanols. However, the same study showed that estradiol permeation was not increased by alkanols of chain length of less than 14 carbon atoms.

Lauryl alcohol is known to be a safe and acceptable ingredient for topical applications. Undiluted lauryl alcohol has been found to be practically non-irritating to the guinea pig. J. F. Treon, "Alcohols in Industrial Hygiene and Toxicology", 2nd ed, vol. II, F. A. Patty (Ed.), Interscience Publishers, New York (1963) p. 1468.

It is well known that the effectiveness of a penetration enhancer depends on the type of drug molecule and the composition of the formulation. Thus, in developing a topical formulation, the identification of an enhancer is only the first step, because reduction in penetration can occur as a multicomponent formulation is developed.

It is an objective of this invention to develop a product having superior skin penetration properties for both an imidazole antifungal agent alone and in combination with steroid anti-inflammatory agent.

SUMMARY OF THE INVENTION

It has now been found that enhanced skin penetration may be achieved in a gel formulation for topical administration comprising a therapeutically effective amount of an imidazole antifungal agent, either by itself or in combination with a steroid anti-inflammatory agent, by including in the vehicle system an effective amount of lauryl alcohol in the absence of propylene glycol. The vehicle also includes a co-solvent system for the imidazole and the steroid which may consist of a lower alkanol, optionally in combination with a trihydroxy alcohol. Such a vehicle may be formed into a gel by the use of a gelling agent such as hydroxypropylcellulose or hydroxyethylcellulose. Such gel formulations may contain 0 to 20% by weight of water. In addition, such gel formulations may also contain appropriate amounts of other pharmaceutically acceptable adjuvants.

DETAILED DESCRIPTION OF THE INVENTION

Figure 1:
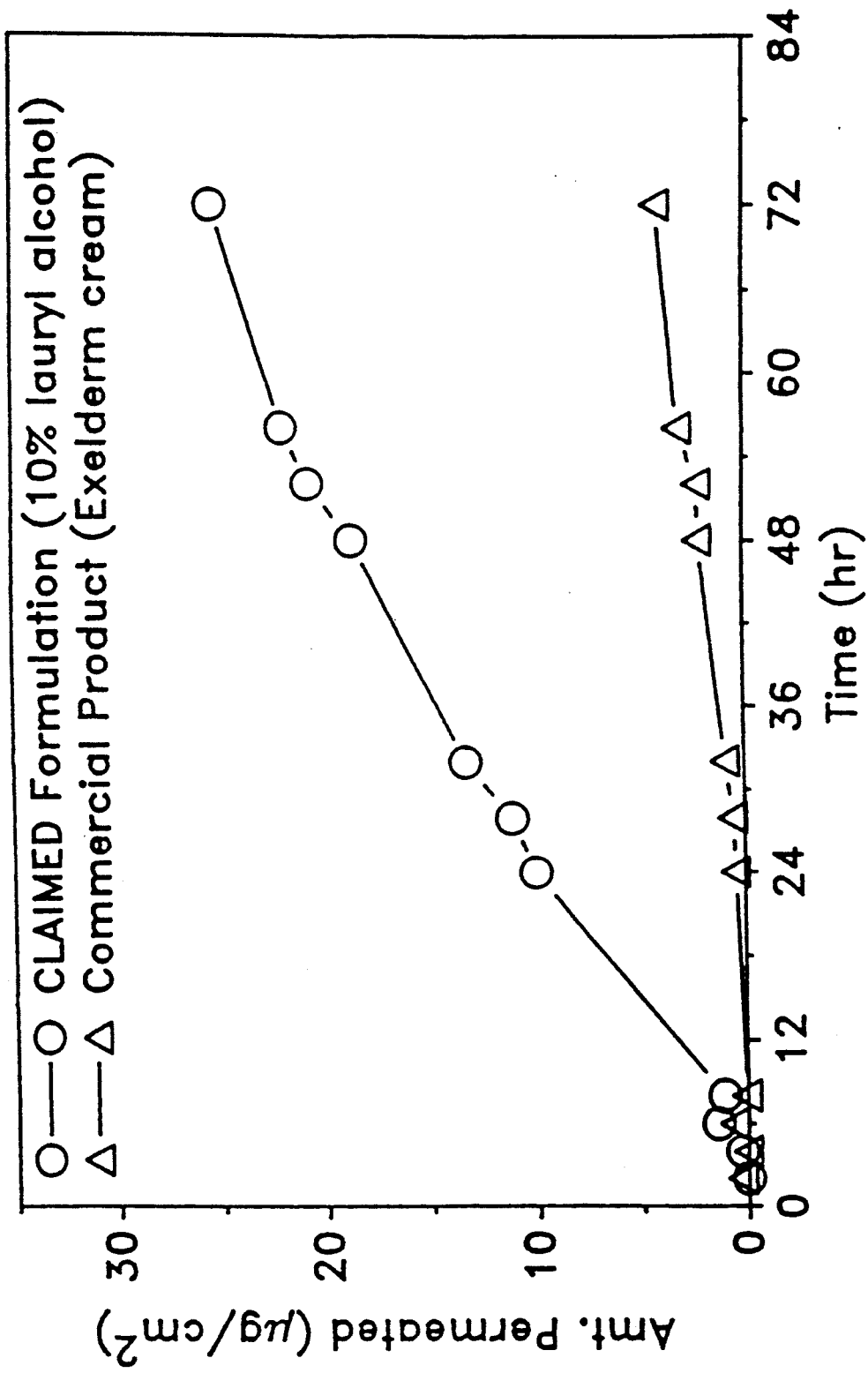
FIG. 1 represents a comparison of the skin permeation of sulconazole nitrate from a gel formulation of the present invention and from a commercial product, "Exelderm" cream.

The topical antifungal formulations of this invention contain 0.1 to 5% w/w, preferably 0.2 to 2.0% w/w, of an imidazole antifungal agent. As used herein the term "imidazole antifungal agent" means any agent having an imidazole functional group in the molecule and possessing topical antifungal activity. A large number of suitable imidazoles have been described in the literature and are well known to those skilled in the art. Examples of suitable imidazole antifungal agents include sulconazole nitrate, econazole nitrate, miconazole nitrate and clotrimazole.

The formulations may also contain an anti-inflammatory steroid, which may be present in a concentration ranging from 0.01 to 2.5% w/w. Examples of steroids which may be used in accordance with this invention are the following: triamcinolone acetonide, hydrocortisone, hydrocortisone acetate, hydrocortisone propionate, hydrocortisone butyrate, hydrocortisone valerate, beclomethasone dipropionate, betamethasone valerate, cortisone acetate, prednisone acetate, prednisone valerate, clocortolone pivalate, dexamethasone, betamethasone dipropionate, halcinonide, flucinolone acetonide, flucinononide, desoximetasone, desonide, betamethasone benzoate, tipredane, halobetasol propionate and clobetasol propionate. Halobetasol propionate and other related steroids are disclosed in U.S. Pat. No. 4,619,921, the disclosure of which is incorporated herein by reference.

Mid-potency steroids are preferred in view of certain disadvantages of strong and low-potency steroids. Strong fluorinated steroids such as betamethasone dipropionate can be cosmetically dangerous to use in intertriginous regions and can cause undesirable effects including skin atrophy, rebound phenomenon and telangiectasia; low potency steroids such as hydrocortisone may fail to provide fast relief of inflammatory symptoms. Examples of suitable mid-potency steroids include hydrocortisone-17-valerate, hydrocortisone-17-butyrate, hydrocortisone-17-propionate, hydrocortisone-17-acetate, betamethasone-17-valerate, cortisone-17-acetate, prednisone-17-acetate, prednisone-17-valerate or triamcinolone acetonide.

The preferred choice for the topical treatment of fungal disease is a combination of a mid-potency steroid and an imidazole antifungal agent. Suitable combinations of mid-potency steroids and imidazole antifungal agents, together with a co-solvent system comprising a lower alkanol in combination with a dihydroxy alcohol, trihydroxy alcohol, or a mixture thereof, are described in U.S. application Ser. No. 323,727, filed Mar. 15, 1989, commonly owned by Bristol-Myers Company, the disclosure of which application is hereby incorporated by reference.

The formulations also contain 1 to 25% w/w, preferably 2.5 to 12% w/w, of lauryl alcohol which is responsible for the superior skin penetrating properties and consequently for the improved antifungal activity. The vehicle system of these formulations is such that both the imidazole antifungal agent and the steroid, if present, are in the solubilized state. The vehicle system consists of, in addition to lauryl alcohol, about 10 to 80% w/w of a lower alkanol, such as ethanol and 0 to 40% w/w of a trihydroxy alcohol such as 1,2,6-hexanetriol. The vehicle system may be formed into a gel by using 0.1 to 5% w/w of a gelling agent such as hydroxypropylcellulose or hydroxyethylcellulose. The formulations may also contain other components conventionally employed in topical preparations, e.g., emollients such as isopropyl myristate, polyoxyethylene (20) polyoxypropylene (5) cetyl ether (PPG-5-cetheth-20), polyoxypropylene (10) methyl glucose ether (PPG-10-methyl glucose ether), polyoxypropylene (20) methyl glucose ether (PPG-20-methyl glucose ether), 2-ethyl-1,3-hexanediol, propylene glycol dioctanoate (PG dioctanoate), methyl gluceth-10, methyl gluceth-20, isodecyl neopentanoate, glycerin, mineral oil, etc. (preferably in an amount of up to about 40% w/w, more preferably about 5 to 30% w/w), and antioxidants such as ascorbyl palmitate, butylated hydroxyanisole (BHA), butylated hydroxytoluene (BHT), etc., chelating agents such as ethylenediaminetetraacetic acid (EDTA), and other preservatives such as salicylic acid, fragrances (up to about 2% w/w), dyes, etc. The pH of the formulation may be adjusted using conventional acids or bases to ensure adequate stability of the imidazole antifungal agent and the steroid, if present.

A general formulation encompassing formulations within the scope of the present invention is set forth below. All amounts are in weight percent.

| General Gel Formula | |
|---|---|
| Component | Amount, % w/w |
| Imidazole antifungal agent | 0.2–2.0 |

-continued

| General Gel Formula | |
| --- | --- |
| Component | Amount, % w/w |
| Steroid anti-inflammatory agent | 0–2.5 |
| Lauryl alcohol | 1–25 |
| Lower alkanol | 10–80 |
| Trihydroxy alcohol | 0–40 |
| Gelling agent | 0.1–5.0 |
| Water | 0–20 |
| Emollient | 0–40 |
| Fragrance | 0–2.0 |
| Preservative | 0–1.5 |

A preferred gel formulation of the present invention containing sulconazole nitrate 1% w/w has the following composition:

| Component | Amount, % w/w |
| --- | --- |
| sulconazole nitrate | 1.0 |
| lauryl alcohol | 10.0 |
| ethyl alcohol | 50.0 |
| 1,2,6-hexanetriol | 26.7 |
| isopropyl myristate | 7.5 |
| PPG-20 methyl glucose ether | 3.0 |
| hydroxypropylcellulose | 0.9 |
| salicylic acid | 0.5 |
| BHA | 0.2 |
| BHT | 0.2 |

A preferred gel formulation of the present invention containing sulconazole nitrate 1% w/w in combination with hydrocortisone-17-valerate 0.2% w/w has the following composition:

| Component | Amount, % w/w |
| --- | --- |
| sulconazole nitrate | 1.0 |
| hydrocortisone-17-valerate | 0.2 |
| lauryl alcohol | 10.0 |
| ethyl alcohol | 50.0 |
| 1,2,6-hexanetriol | 26.5 |
| isopropyl myristate | 7.5 |
| PPG-20 methyl glucose ether | 3.0 |
| hydroxypropylcellulose | 0.9 |
| salicylic acid | 0.5 |
| BHA | 0.2 |
| BHT | 0.2 |

The pH of the above formulation is adjusted to 4.0 with 1N solution of sodium hydroxide.

Topical treatment of a fungal infection involves applying an antifungal formulation directly to the skin at the site of the infection. The efficacy of the antifungal formulation depends on the extent to which the antifungal agent penetrates into the skin. In U.S. Pat. No. 4,775,678, Su et al, it is demonstrated that increasing the skin permeation of clotrimazole results in substantially improved antifungal activity against Trichophyton mentagrophytes in a guinea pig dermatophyte model.

The in vitro skin permeation of sulconazole nitrate 1% w/w from the preferred gel formulation of the present invention (example 2, below) and from a commercial cream, i.e., "Exelderm" marketed by Westwood Pharmaceuticals, was compared and the results are shown in FIG. 1. The permeation experiments were carried out using excised human skin and Franz diffusion cells. The data in FIG. 1 shows that the rate of skin permeation and the amount of sulconazole nitrate permeated across the skin are about 5 times greater from the topical formulation of this invention than from the commercial formulation, Exelderm cream.

Figure 2:
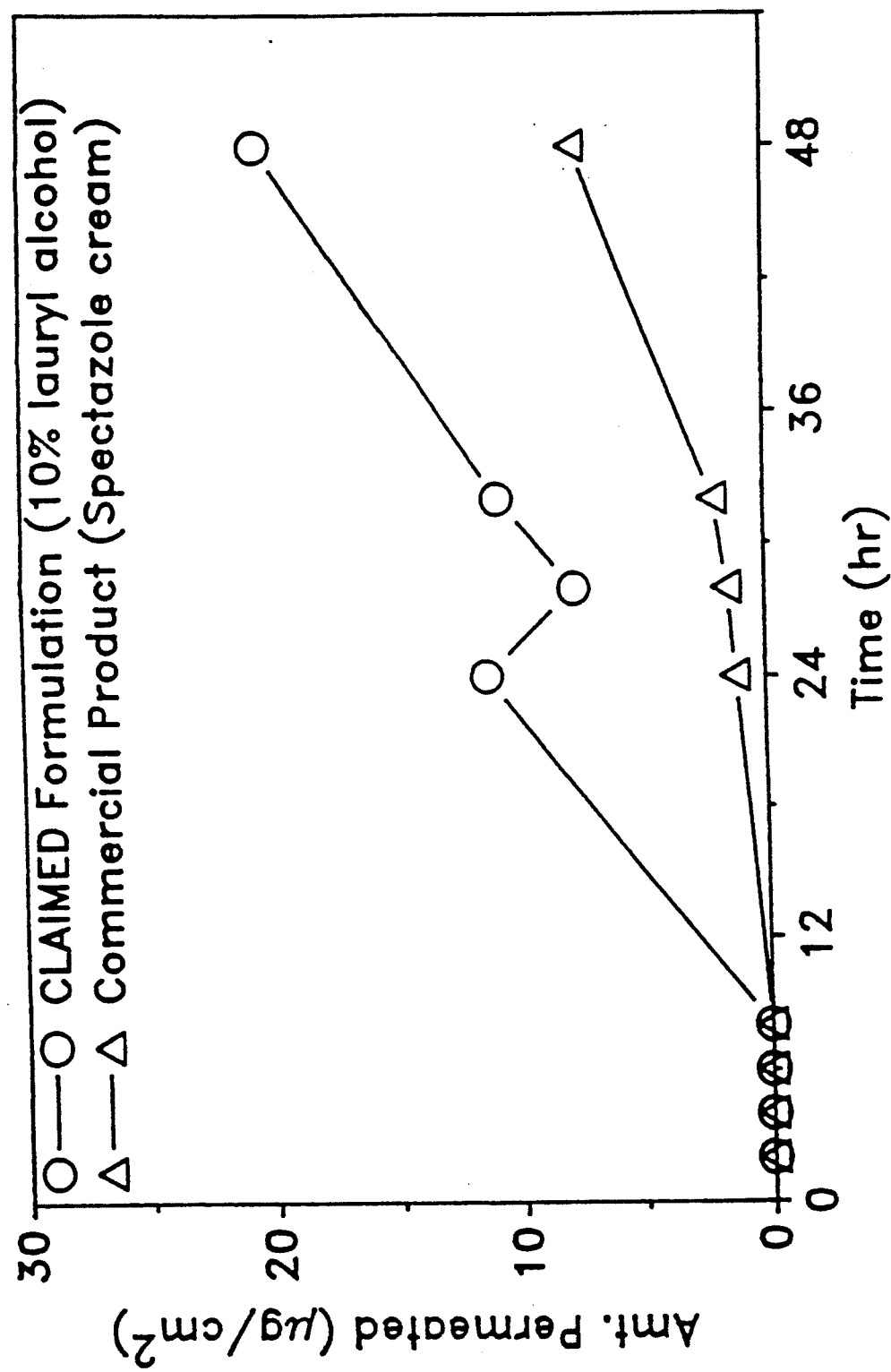
FIG. 2 represents a comparison of the skin permeation of econazole nitrate from a gel formulation of the present invention and from a commercial product, "Spectazole" cream.
Figure 3:
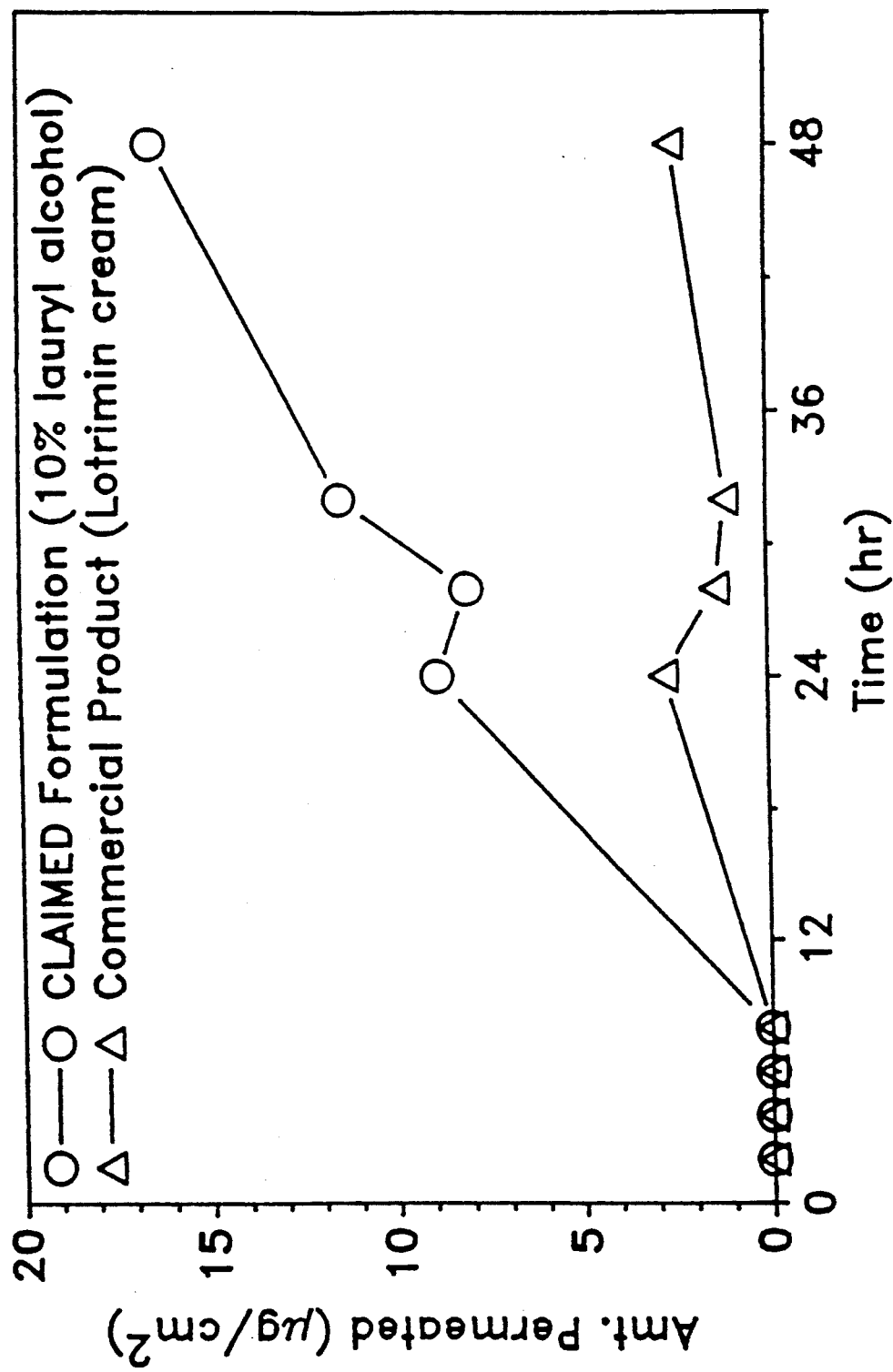
FIG. 3 represents a comparison of the skin permeation of clotrimazole from a gel formulation of the present invention and from a commercial product, "Lotrimin" cream.

Similarly, the skin permeation of two other imidazole antifungal agents, econazole nitrate 1% w/w and clotrimazole 1% w/w, was found to be about 3-6 times greater from the topical formulation of the present invention (examples 3 and 4, below) as compared to the commercially marketed products, i.e., "Spectazole" cream containing 1% econazole nitrate and marketed by Ortho Pharmaceutical Corp., and "Lotrimin" cream containing 1% w/w clotrimazole and marketed by Schering Corp. The skin permeation profiles of econazole nitrate and clotrimazole are shown in FIG. 2 and FIG. 3, respectively.

The skin permeation rates and the amount permeated are listed in Table 1.

TABLE 1

| | Permeation Rate ($\mu g/cm^2$-hr) | | Amt. Permeated at the end of 48 hr ($\mu g/cm^2$) | |
| --- | --- | --- | --- | --- |
| Antifungal Agent | Claimed Formulation | Commercial Product | Claimed Formulation | Commercial Product |
| Sulconazole nitrate | 0.377 | 0.078 | 25.32 | 4.09 |
| Econazole nitrate | 0.983 | 0.122 | 20.45 | 7.60 |
| Clotrimazole | 0.345 | 0.065 | 16.43 | 2.50 |

The topical antifungal formulation of the present invention having superior skin penetration properties would have a number of advantages over currently available products. It may allow treatment of deep skin fungal infections which cannot be effectively treated by currently available topical products. Such a formulation delivering a higher amount of antifungal agent into the skin may also permit a once-a-day treatment regimen, thus increasing patient convenience and compliance. In addition, a formulation with a lower concentration of antifungal agent, but with superior penetration properties, could be used for superficial fungal infections of the skin.

The following examples illustrate the invention.

EXAMPLE 1

| EXAMPLE 1 | |
| --- | --- |
| Component | Amount, % w/w |
| sulconazole nitrate | 1.0 |
| hydrocortisone-17-valerate | 0.2 |
| lauryl alcohol | 10.0 |
| ethyl alcohol | 50.0 |
| 1,2,6-hexanetriol | 26.5 |
| isopropyl myristate | 7.5 |
| PPG-20 methyl glucose ether | 3.0 |
| hydroxypropylcellulose | 0.9 |
| salicylic acid | 0.5 |
| BHA | 0.2 |
| BHT | 0.2 |

Procedure

Dissolve sulconazole nitrate, hydrocortisone-17-valerate, salicylic acid, BHA and BHT in the ethyl alcohol with stirring. Add the hydroxypropylcellulose and allow to gel with rapid stirring for 1-2 hr. Add the isopropyl myristate, PPG-20 methyl glucose ether and 1,2,6-hexanetriol and mix until uniform.

The following examples are prepared according to the procedure for Example 1.

EXAMPLE 2

| Component | Amount, % w/w |
|---|---|
| sulconazole nitrate | 1.0 |
| lauryl alcohol | 10.0 |
| ethyl alcohol | 50.0 |
| 1,2,6-hexanetriol | 26.7 |
| isopropyl myristate | 7.5 |
| PPG-20 methyl glucose ether | 3.0 |
| hydroxypropylcellulose | 0.9 |
| salicylic acid | 0.5 |
| BHA | 0.2 |
| BHT | 0.2 |

EXAMPLE 3

| Component | Amount, % w/w |
|---|---|
| econazole nitrate | 1.0 |
| lauryl alcohol | 10.0 |
| ethyl alcohol | 50.2 |
| 1,2,6-hexanetriol | 26.5 |
| isopropyl myristate | 7.5 |
| PPG-20 methyl glucose ether | 3.0 |
| hydroxypropylcellulose | 0.9 |
| salicylic acid | 0.5 |
| BHA | 0.2 |
| BHT | 0.2 |

EXAMPLE 4

| Component | Amount, % w/w |
|---|---|
| clotrimazole | 1.0 |
| lauryl alcohol | 10.0 |
| ethyl alcohol | 50.2 |
| 1,2,6-hexanetriol | 26.5 |
| isopropyl myristate | 7.5 |
| PPG-20 methyl glucose ether | 3.0 |
| hydroxypropylcellulose | 0.9 |
| salicylic acid | 0.5 |
| BHA | 0.2 |
| BHT | 0.2 |

EXAMPLE 5

| Component | Amount, % w/w |
|---|---|
| sulconazole nitrate | 1.0 |
| lauryl alcohol | 10.0 |
| ethyl alcohol | 50.0 |
| 1,2,6-hexanetriol | 26.7 |
| 2-ethyl-1,3-hexanediol | 7.5 |
| PPG-20 methyl glucose ether | 3.0 |
| hydroxypropylcellulose | 0.9 |
| salicylic acid | 0.5 |
| BHA | 0.2 |
| BHT | 0.2 |

EXAMPLE 6

| Component | Amount, % w/w |
|---|---|
| sulconazole nitrate | 1.0 |
| hydrocortisone-17-valerate | 0.2 |
| lauryl alcohol | 5.0 |
| ethyl alcohol | 50.0 |
| 1,2,6-hexanetriol | 31.5 |
| isopropyl myristate | 7.5 |
| PPG-20 methyl glucose ether | 3.0 |
| hydroxypropylcellulose | 0.9 |
| salicylic acid | 0.5 |
| BHA | 0.2 |
| BHT | 0.2 |

The pH of the above formulation is adjusted to between 3.5–4.5 with 1M sodium hydroxide.

EXAMPLE 7

| Component | Amount, % w/w |
|---|---|
| sulconazole nitrate | 1.0 |
| hydrocortisone-17-valerate | 0.2 |
| lauryl alcohol | 2.5 |
| ethyl alcohol | 50.0 |
| 1,2,6-hexanetriol | 34.0 |
| isopropyl myristate | 7.5 |
| PPG-20 methyl glucose ether | 3.0 |
| hydroxypropylcellulose | 0.9 |
| salicylic acid | 0.5 |
| BHA | 0.2 |
| BHT | 0.2 |

The pH of the above formulation is adjusted to between 3.5–4.5 with 1M sodium hydroxide.

We claim:

1. A penetration-enhancing gel formulation for topical administration that does not contain propylene glycol comprising:
   (a) a therapeutically effective amount of an imidazole antifungal agent,
   (b) a solvent system consisting essentially of a lower alkanol, optionally in combination with a trihydroxy alcohol,
   (c) an effective amount of a gelling agent, and
   (d) an effective amount of lauryl alcohol to enhance skin penetration.

2. The gel formulation according to claim 1 which also includes water in an amount up to about 20% by weight.

3. A gel formulation for topical administration that does not contain propylene glycol comprising:
   (a) from about 0.1 to 5% by weight of an imidazole antifungal agent,
   (b) from about 0% to 20% by weight of water,
   (c) from about 10% to 80% by weight of lower alkanol solvent,
   (d) from about 0% to 40% by weight of a trihydroxy alcohol solvent,
   (e) from about 0.1% to 5% by weight of a gelling agent selected from the group consisting of hydroxypropylcellulose and hydroxyethylcellulose, and
   (f) from about 1.0% to 25% by weight of lauryl alcohol.

4. The gel formulation of claim 3 wherein said imidazole antifungal agent is in the amount of about 0.2% to 2% by weight.

5. The gel formulation of claim 4 which further contains up to about 40% by weight of an emollient.

6. The gel formulation of claim 5 wherein said emollient is selected from the group consisting of isopropyl myristate, polyoxyethylene (20) polyoxypropylene (5) cetyl ether, polyoxypropylene (10) methyl glucose ether, polyoxypropylene (20) methyl glucose ether, 2-ethyl-1,3-hexanediol, propylene glycol dioctanoate, methyl gluceth-10, methyl gluceth-20, isodecyl neopentanoate, glycerin, and mineral oil.

7. The gel formulation of claim 4 which further contains an effective amount of a preservative.

8. The gel formulation of claim 7 wherein said preservative is ascorbyl palmitate, butylated hydroxytoluene, butylated hydroxyanisole, ethylenediaminetetraacetic acid, salicylic acid, or a combination thereof.

9. The gel formulation of claim 4 which further contains a fragrance.

10. A stable penetration-enhancing gel formulation for topical administration that does not contain propylene glycol comprising:
    (a) a therapeutically effective amount of a mixture of an imidazole antifungal agent and a steroid anti-inflammatory agent,
    (b) a solvent system consisting essentially of a lower alkanol, optionally in combination with a trihydroxy alcohol,
    (c) an effective amount of a gelling agent, and
    (d) an effective amount of lauryl alcohol to enhance skin penetration.

11. The gel formulation according to claim 4 which also includes water in an amount up to about 20% by weight.

12. A gel formulation for topical administration that does not contain propylene glycol comprising:
    (a) from about 0.1% to 5% of an imidazole antifungal agent,
    (b) from about 0.01% to 2.5% by weight of a steroid anti-inflammatory agent,
    (c) from about 10% to 80% by weight of a lower alkanol solvent,
    (d) from about 0% to 40% by weight of a trihydroxy alcohol solvent,
    (e) from about 0% to 20% by weight of water,
    (f) from about 0.1% to 5% by weight of a gelling agent selected from the group consisting of hydroxypropylcellulose and hydroxyethylcellulose, and
    (g) from about 1.0% to about 25% by weight of lauryl alcohol.

13. The gel formulation of claim 12 wherein said imidazole antifungal agent is in the amount of about 0.2% to 2.0% by weight.

14. The gel formulation of claim 12 which further contains up to about 40% of an emollient.

15. The gel formulation of claim 14 wherein said emollient is selected from the group consisting of isopropyl myristate, polyoxyethylene (20) polyoxypropylene (5) cetyl ether, polyoxypropylene (10) methyl glucose ether, polyoxypropylene (20) methyl glucose ether, 2-ethyl-1,3-hexanediol, propylene glycol dioctanoate, methyl gluceth-10, methyl gluceth-20, isodecyl neopentanoate, glycerin, and mineral oil.

16. The gel formulation of claim 12 which further contains an effective amount of a preservative.

17. The gel formulation of claim 16 wherein said preservative is ascorbyl palmitate, butylated hydroxytoluene, butylated hydroxyanisole, ethylenediaminetetraacetic acid, salicylic acid or a combination thereof.

18. The gel formulation of claim 12 wherein said steroid anti-inflammatory agent is a mid-potency steroid.

19. The gel formulation of claim 18 wherein said steroid anti-inflammatory agent is selected from the group consisting of hydrocortisone-17-valerate, hydrocortisone-17-butyrate, hydrocortisone17-propionate, hydrocortisone-17-acetate, betamethasone-17-valerate, cortisone-17-acetate, prednisone-17-acetate, prednisone-17-valerate and triamcinolone acetonide.

20. A gel formulation for topical administration that does not contain propylene glycol comprising the following:

| Component | Amount, % w/w |
| --- | --- |
| Imidazole antifungal agent | 0.2–2.0 |
| Steroid anti-inflammatory agent | 0–2.5 |
| Lauryl alcohol | 1–25 |
| Lower alkanol | 10–80 |
| Trihydroxy alcohol | 0–40 |
| Gelling agent | 0.1–5.0 |
| Water | 0–20 |
| Emollient | 0–40 |
| Fragrance | 0–2.0 |
| Preservative | 0–1.5 |

21. A gel formulation for topical administration that does not contain propylene glycol having substantially the following formula:

| Component | Amount, % w/w |
| --- | --- |
| sulconazole nitrate | 1.0 |
| lauryl alcohol | 10.0 |
| ethyl alcohol | 50.0 |
| 1,2,6-hexanetriol | 26.7 |
| isopropyl myristate | 7.5 |
| polyoxypropylene (20) methyl glucose ether | 3.0 |
| hydroxypropylcellulose | 0.9 |
| salicylic acid | 0.5 |
| butylated hydroxyanisole | 0.2 |
| butylated hydroxytoluene | 0.2 |

22. A gel formulation for topical administration that does not contain propylene glycol having substantially the following formula:

| Component | Amount, % w/w |
| --- | --- |
| sulconazole nitrate | 1.0 |
| hydrocortisone-17-valerate | 0.2 |
| lauryl alcohol | 10.0 |
| ethyl alcohol | 50.0 |
| 1,2,6-hexanetriol | 26.5 |
| isopropyl myristate | 7.5 |
| polyoxypropylene (20) methyl glucose ether | 3.0 |
| hydroxypropylcellulose | 0.9 |
| salicylic acid | 0.5 |
| butylated hydroxyanisole | 0.2 |
| butylated hydroxytoluene | 0.2 | the pH of the above formulation being adjusted to 4.0 with 1M solution of sodium hydroxide.

* * * * *